United States Patent
Vasta et al.

(10) Patent No.: US 6,881,344 B2
(45) Date of Patent: Apr. 19, 2005

(54) METHOD FOR SETTING UP A DIALYSIS TREATMENT IN A DIALYSIS MACHINE

(75) Inventors: Alessandro Vasta, Modena (IT); Fabio Govoni, Renazzo (IT)

(73) Assignee: Gambro Dasco S.p.A., Medolla (IT)

( * ) Notice: Subject to any disclaimer, the term of this patent is extended or adjusted under 35 U.S.C. 154(b) by 435 days.

(21) Appl. No.: 10/088,389

(22) PCT Filed: Jul. 19, 2001

(86) PCT No.: PCT/IB01/01288

§ 371 (c)(1),
(2), (4) Date: Aug. 12, 2002

(87) PCT Pub. No.: WO02/07796

PCT Pub. Date: Jan. 31, 2002

(65) Prior Publication Data

US 2003/0073950 A1 Apr. 17, 2003

(30) Foreign Application Priority Data

Jul. 21, 2000 (IT) .................................... TO2000A0728

(51) Int. Cl.⁷ .......................... B01D 61/32; B01D 61/28
(52) U.S. Cl. ........................ 210/646; 210/85; 210/102; 210/134; 210/141; 210/143; 210/321.65; 210/321.71; 210/96.2; 210/645; 210/739; 210/929; 604/28; 604/29; 702/85
(58) Field of Search ................. 210/85, 102, 134, 210/141, 143, 96.2, 321.65, 321.71, 645, 646, 739, 929; 604/28, 29; 702/19, 85, FOR 119

(56) References Cited

U.S. PATENT DOCUMENTS 5,620,608 A  4/1997  Rosa et al. ................. 210/739

FOREIGN PATENT DOCUMENTS

EP          0 623 357 A1    11/1994
WO          WO98/35747      8/1998

Primary Examiner—John Kim
(74) Attorney, Agent, or Firm—Finnegan, Henderson, Farabow, Garrett & Dunner, L.L.P.

(57) ABSTRACT

A method of setting up a dialysis treatment in a dialysis machine (1) provided with a device (6) for setting up the dialysis treatment, possessing a microprocessor (11), a data input (12, 13) and a screen (13), comprises the steps of: supplying a group of functions (U(t, P); C(t, P)) of a quantity (U; C) that is characteristic of the dialysis treatment as a function of time (t) and of a parameter (P) correlated with intermediate values ($U_1$, $C_1$) of each function (U(t; P); C(t; P)) of the group; selecting a subset of the group of functions (U(t, P); C(t; P)) imposing boundary conditions ($U_0$, TWL, DT; $C_0$, $C_f$, DT; $C_0$, CS, DT) that are characteristic of a particular therapy; assigning values to the parameter (P) and displaying the curves corresponding to the functions (U(t, P); C(t, P)) of the subset and to the respective values assigned to parameter (P); and selecting one of the functions ((U(t, P); C(t, P)) of the subset on the basis of the images of the curves.

18 Claims, 3 Drawing Sheets

Fig. 8

METHOD FOR SETTING UP A DIALYSIS TREATMENT IN A DIALYSIS MACHINE

The present invention relates to a method of setting up a dialysis treatment in a dialysis machine.

In general, dialysis machines are preset for carrying out dialysis treatments that are personalized for patients affected by renal insufficiency. In other words, the dialysis machines have control devices that make it possible to set up a dialysis treatment that is specific to each patient on the basis of the medical instructions. As a rule, a prescription for a patient affected by renal insufficiency and undergoing dialysis treatment comprises instructions relating to the weight loss that the patient should experience and to the amount of salts that the patient should receive in the form of ions during the dialysis treatment. Other data characterizing the dialysis treatment, such as the maximum weight loss in unit time tolerated by the patient and the duration of the dialysis treatment, can be obtained from the general conditions of health and from the patient's physical characteristics. The weight loss during a dialysis treatment is due to expulsion of a proportion of the blood fluid.

For this purpose, a dialysis machine of known type comprises an extracorporeal blood circuit connected, in use, to the patient's circulatory system, a dialysate circuit, and a filter through which the blood circuit conveys the blood fluid and the dialysate circuit conveys the dialysate. The filter comprises a semipermeable membrane, which separates, in use, the dialysate from the blood fluid and permits an exchange of ions between the dialysate and the blood fluid and the transfer of a proportion of the blood fluid through the membrane. The machine further comprises an ultrafiltration pump for expelling a defined quantity of the patient's blood fluid from the dialysate circuit and through the membrane to achieve the aforesaid weight loss. Therefore there is a biunique correspondence between the weight loss and the quantity of blood fluid expelled during the whole treatment and, similarly, between the weight loss in unit time, also called the rate of weight loss, and the delivery of the ultrafiltration pump. However, this correspondence is not valid in the case where the extracorporeal circuit is provided with an infusion bag that releases a flow of infusion fluid into the blood circuit. In this case the weight loss in unit time will be equal to the difference between the ultrafiltration flow rate and the infusion flow rate.

The extent of ion exchange is a function of the concentration of salts in the blood fluid and of the natraemia of the patient's blood fluid. In other words, the quantity of salts transferred to the patient is determined by setting the concentration of ions of the dialysate and depends on the ion concentration and on the conditions of the blood fluid. The concentration of the dialysate is measured by determining the conductivity of the dialysate and is monitored during the dialysis treatment.

In less recent dialysis machines, the values of the weight loss in unit time and of the conductivity of the dialysate were kept constant throughout the treatment and were kept relatively low owing to the fact that the patient was unable to tolerate high values, and in consequence the dialysis treatments were extremely long.

The newer dialysis machines are provided with devices for setting up the treatment, in which the values of the weight loss in unit time and of the concentration of salts in the dialysate are set in such a way that they vary as a function of time. This innovation in the field of dialysis machines occurred as a result of research in which it was found that a high weight loss in unit time can be tolerated well by an average patient in the initial stage of treatment, whereas the critical stage with regard to the weight loss in unit time is the final stage of treatment, during which the patient has already lost a large part of the weight, in the form of blood fluid, and is able to tolerate a weight loss in unit time that is relatively low compared with the initial weight loss in unit time. Furthermore, research has also shown that the patient's receptiveness to the administration of salts in the form of ions is greater in the final stage of treatment compared with the patient's receptiveness in the initial stage of the treatment. Thus, the data setting devices of the newest machines have adapted to the innovations introduced by medical research and make it possible to define both the function of the weight loss in unit time as a function of time, and the function of the conductivity of the solution of dialysate as a function of time.

Existing devices for setting up a dialysis treatment are based on various methods, some of which envisage the introduction of data on weight loss in unit time for a series of successive intervals of time of the treatment, so that a histogram is substantially defined. In the same way, conductivity data are introduced for a series of time intervals so as to define a histogram. Determination of a histogram makes it possible to define the parameters of the dialysis treatment with increasing precision as the time intervals become shorter, so that the dialysis treatment can be tailored very accurately to the requirements of a given patient. However, these methods require the input of a value for each bar of the histogram, and for this reason it takes a relatively long time to set up the dialysis treatment.

Other less refined methods envisage the setting of only the initial values and final values of weight loss in unit time and of the conductivity of the dialysate solution and the duration of the dialysis treatment and constantly varying the weight loss in unit time and the conductivity between the initial value and the final value. The setting-up time is much shorter for these methods, but they do not permit the setting up of optimum treatments for each patient.

The aim of the present invention is to provide a method of setting up a dialysis treatment in a dialysis machine that does not have the disadvantages of the prior art and, in particular, is accurate, increases the efficiency of the treatment and at the same time can be implemented easily and quickly.

According to the present invention, a method is provided for setting up a dialysis treatment in a dialysis machine provided with a device for setting up the dialysis treatment comprising a microprocessor, a data input and a screen, the method comprising the steps of:

supplying a group of functions of a quantity that is characteristic of the dialysis treatment as a function of time and of a variable parameter correlated with intermediate values of each function in the group;

selecting a subset of the group of functions imposing boundary conditions that are characteristic of a particular therapy;

assigning values to the parameter and displaying the curves corresponding to the functions of the subset and to the respective values assigned to the parameter; and selecting one of the functions of the subset on the basis of the images of the curves.

The present invention will now be described with reference to the accompanying drawings, which illustrate one non-limitative embodiment thereof, in which.

Figure 1:
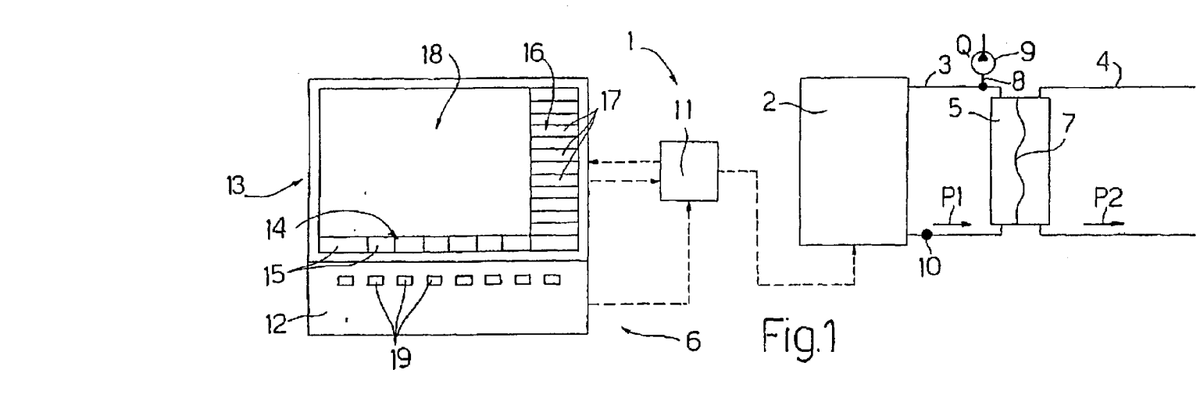
FIG. 1 is a schematic view of a dialysis machine constructed according to the present invention.

Referring to FIG. 1, 1 indicates the whole dialysis machine for providing dialysis treatments for patients affected by renal insufficiency. Machine 1 comprises apparatus 2 for preparing the dialysate, a dialysate circuit 3, a blood circuit 4, a filter 5 and a device 6 for setting up the dialysis treatment. Dialysate circuit 3 transports the dialysate along a path P1 through filter 5 and is connected to apparatus 2, whereas the blood circuit 4, in use, is connected to the circulatory system of a patient and conveys the blood fluid along a path P2 through filter 5, in which the dialysate fluid and the blood fluid are separated by a semipermeable membrane 7, across which the ions of the dialysate fluid are transferred to the blood fluid, whereas the impurities contained in the blood fluid are transferred to the dialysate. The degree of exchange depends on the ion concentration of the dialysate and on the natraemia of the patient's blood fluid. Along circuit 3, downstream from filter 5, there is a branch 8 for extraction of blood fluid and an ultrafiltration pump 9 for extracting a flow rate Q of blood fluid, which passes through filter 5. In practice, ultrafiltration pump 9 provides extraction of the part of the blood fluid that crosses the semipermeable membrane 7, and in this way produces the patient's weight loss. Apparatus 2 provides supply of the concentration of salts in the form of ions to the dialysate, whereas a sensor 10 mounted on dialysate circuit 3 detects the electrical conductivity C of the dialysate, the electrical conductivity C being correlated to the concentration of ions in the dialysate. Apparatus 2 and ultrafiltration pump 9 are controlled by a control unit (not shown), which determines the variation of the concentration of salts and of the delivery Q of the ultrafiltration pump 9.

Device 6 comprises a microprocessor 11, a keyboard 12 and a screen 13, which is interactive, of the "touch screen" type, and is subdivided into a zone 14, in which there are touch keys 15 for navigating and for selecting the pages of an electronic notebook, a zone 16, with touch keys 17 for controlling apparatus 2, and a zone 18 for displaying the values for setting up the dialysis treatment and the characteristic curves of the dialysis treatment. Keyboard 12 includes hard keys 19, which include a key 19 for going into a SET MODE for setting up the dialysis treatment, a key 19 "+/−" for changing the values of the data for setting up the dialysis treatment, and a key 19 for confirming the data.

Figure 2:
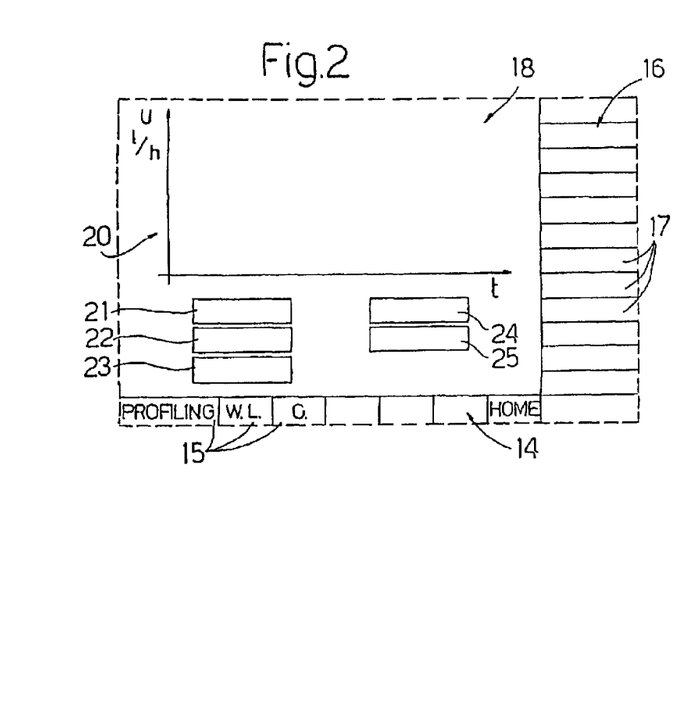
FIGS. 2 to 7 are images displayed by a screen of the dialysis machine of FIG. 1 during setting up of a dialysis treatment.

On selecting key 19 for access to the SET MODE, keys 15 appear, indicating PROFILING, "WL", i.e. the option for setting the weight loss, and "C", i.e. setting of conductivity. Two keys 17 permit selection of the modes "PC" (PROGRESSIVE CURVE) and "STEP" (histogram), which permit access respectively to the mode for selection of a curve of variation of the rate of weight loss as a function of time without discontinuities in the first derivative and to a mode for setting a histogram, of a known type, of variation of the rate of weight loss as a function of time. Selection of key 17 "PC" supplies the image illustrated in FIG. 2 and includes a cartesian system 20, which shows time t on the ordinate and, on the abscissa, the hourly weight loss U expressed in kg/h, a box/touch key 21 for input of the figure for total weight loss TWL, a box/touch key 22 for input of the dialysis time DT, a box 23 for displaying that operation is in progressive curve mode, a box/touch key 24 for input of the initial value of weight loss in unit time, i.e. the maximum weight loss $U_0$ and a box/touch key 25 for input of a parameter P, which characterizes the shape of the progressive curve. In use, the operator touches box/key 21, which becomes activated, and by means of key 19 "+/−" alters a predefined value of the total weight loss TWL until box/key 21 displays the value of the total weight loss TWL defined by the therapy, and the operator confirms that value by means of confirmation key 19. In a similar manner, by using boxes/touch keys 22 and 24 and keys 19, the operator inputs and confirms the values of DT and of $U_0$, respectively.

Once the operator has selected the "progressive curve" mode, microprocessor 11 makes reference to a group of predefined functions U(t, P) characterizing the weight loss in unit time and parametrized, with parameter P. The group of functions U(t,P) comprises a family of straight lines AA, a family of parabolas BB with their convexity pointing upwards, and a family of hyperbolas CC with their convexity pointing downwards. As an example, below are given the families of functions U(t,P) that reflect the shapes of curves AA, BB and CC respectively.

Functions U(t;P) with a straight-line relationship corresponding to the family of straight lines AA $$U = K \cdot t + U_0;$$

functions U(t,P) with a course with convexity upwards corresponding to the family of parabolas BB $$U = A \cdot t^2 + B \cdot t + U_0;$$

functions U(t,P) with a course with convexity downwards corresponding to the family of hyperbolas CC $$U = \frac{D}{E + F \cdot t + t^2}$$

The progressive curve AA, BB, CC that is to be preselected corresponds to a function U(t) of the group stated above and depends on the value assigned to the discriminating parameter P, which indicates the curvature of the curve relating the value $U_0$ of the initial weight loss to a value of the final weight loss $U_f$ for t=DT, and the value of the intermediate weight loss $U_i$ for t=DT/2 according to the following relation:

$$U_i = U_f + P \cdot \frac{U_0 - U_f}{100}$$

in which P is expressed as a percentage and $U_f$ is an unknown and is always less than $U_0$, representing the maximum weight loss tolerated by the patient. In other words, the intermediate value $U_i$ of the weight loss is determined by parameter P.

Although the value of $U_f$ is unknown, the value of P equal to fifty percent indicates that the curve belongs to the family of straight lines AA, and microprocessor 11 calculates the value of K, imposing the following condition:

$$TWL = \int_0^{DT} (K \cdot t + U_0) \cdot dt$$

Figure 3:
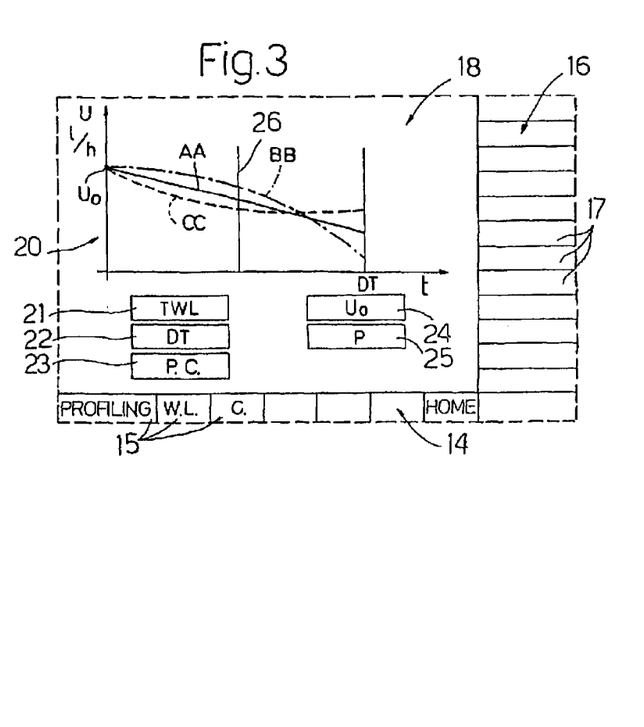

This condition means that the total weight loss is equal to the area subtended by a straight line belonging to the family of straight lines AA for determining coefficient K. Once the value of coefficient K is known, microprocessor 11 calculates the values of the flow U as a function of t and displays the straight line in the system of cartesian axes 20 as shown in FIG. 3.

Parameter P is variable over a range of variability between twenty and eighty percent and for values of P greater than fifty percent the curve belongs to the family of parabolas BB, whereas for values of P less than fifty percent the curve belongs to the family of hyperbolas CC. This range of variability also requires that the value of $U_i$ is always between the value $U_0$ and the value $U_f$.

Microprocessor 11 determines the coefficients A and B of the parabola for each value of P between fifty percent and eighty percent, imposing the following conditions:

$$U_i = A \cdot \left(\frac{DT}{2}\right)^2 + B \cdot \frac{DT}{2} + U_0 \text{ for } t = DT/2;$$

$$U_f = A \cdot DT^2 + B \cdot DT + U_0 \text{ for } t = DT;$$

$$U_i = U_f + P \cdot \frac{U_0 - U_f}{100} \text{ for } 50 < P < 80;$$

$$TWL = \int_0^{DT} (A \cdot t^2 + B \cdot t + C) \cdot dt.$$

In the four-equation system, the values DT, TWL, $U_0$ and P are known, whereas the unknowns are $U_f$, $U_i$, A and B, which vary as coefficient P varies.

Substantially similarly, the coefficients D, E, and F of the hyperbola are determined by microprocessor 11 for each value of parameter P between fifty percent and 20 percent with the following system of equations:

$$U_{0=D/E} \text{ per } t=0;$$

$$U_i = \frac{D}{E + F \cdot \frac{DT}{2} + \left(\frac{DT}{2}\right)^2} \text{ for } t = DT/2;$$

$$U_f = \frac{D}{E + F \cdot DT + DT^2} \text{ for } t = DT;$$

$$U_i = U_f + P \cdot \frac{U_0 - U_f}{100} \text{ for } 20 < P < 50;$$

$$TWL = \int_0^{DT} \left(\frac{D}{E + F \cdot t + t^2}\right) \cdot dt.$$

In the five-equation system, the values DT, TWL, $U_0$ and P are known, whereas the unknowns are $U_f$, $U_i$, D, E and F, which vary with variation of coefficient P.

In practice, once we have predefined the group of functions U(t;,P):

$$U = K \cdot t + U_0;$$

$$U = A \cdot t^2 + B \cdot t + U_0;$$

$$U = \frac{D}{E + F \cdot t + t^2}$$

the imposing of boundary conditions TWL, $U_0$, and DT selects a subset of the group of functions U(t,P) whereas assignment of a defined value to parameter P isolates a single function U(t) from the subset, so that the systems of equations become defined.

From the operational standpoint, once the values TWL, $U_0$ and DT have been assigned, the operator varies parameter P by touching the box/touch key 25 and key 19 "+/−" and microprocessor 11 displays, on screen 13, the curve corresponding to the value assigned to parameter P and displayed in the respective box/key 25. Referring to FIG. 3, each curve displayed satisfies the values TWL, $U_0$, and DT established on the basis of the doctor's prescription, therefore from the quantitative standpoint the therapeutic values are satisfied. The operator can select the qualitative course of administration for each patient by visually selecting the curve that belongs to one of the families AA, BB, CC and is best suited to the characteristics of the given patient by varying parameter P. Together with the system of cartesian axes 20, a bar 26 is displayed, which is parallel to the ordinate, is positioned to correspond to the value DT/2, and intercepts the curve at point $U_i$.

Figure 4:
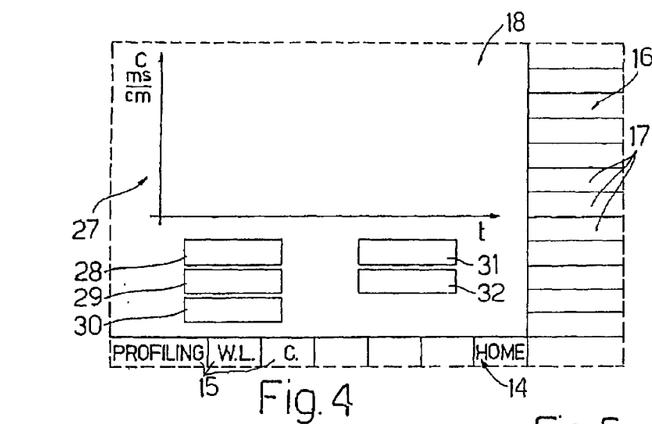

The course of the concentration C(t) of the dialysate as a function of time is determined similarly. In this case, screen 13 supplies the image of FIG. 4 which shows a cartesian system 27, which has an abscissa showing the scale for time t and an ordinate showing the scale for conductivity C expressed in mS/cm (millisiemens per centimeter), a box/touch key 28 for input of the initial and maximum conductivity $C_0$, a box/touch key 29 for input of the final conductivity $C_f$, a box 30 for displaying the progressive curve mode, a box/touch key 31 for inputting the dialysis time DT and a box/touch key 32 for inputting parameter P.

With variation of parameter P, the progressive curve belongs to a family of straight lines A1 for P equal to fifty percent, to a family of parabolas B1 with convexity upwards for P for a value greater than fifty percent, and to a family of hyperbolas C1 for a value of P less than fifty percent.

Functions C(t) with a straight-line course corresponding to the family of straight lines A1 for P equal to 50% are as follows:

$$C = K \cdot t + C_0;$$

functions C(t) corresponding to the family of curves B1 are as follows:

$$C = A \cdot t^2 + B \cdot t + C_0;$$

functions C(t) corresponding to the family of curves C1 are as follows:

$$C = \frac{D}{E + F \cdot t + t^2}.$$

In this case there is a change in boundary conditions for determining the unknowns. With regard to the straight line it is stipulated that $$C_f = KDT + C_0 \text{ for } t=DT;$$

in which the unknown is K, whereas $C_f$, DT and $C_0$ are known.

For a value of P greater than fifty percent the curve belongs to the family of parabolas B1 and the following conditions are imposed:

$$C_i = A \cdot \left(\frac{DT}{2}\right)^2 + B \cdot \frac{DT}{2} + C_0 \text{ for } t = DT/2;$$

$$C_f = A \cdot DT^2 + B \cdot DT + C_0 \text{ for } t = DT;$$

$$C_i = U_f + P \cdot \frac{C_0 - C_f}{100} \text{ for } 50 < P < 80$$

In the three-equation system, A, B and $C_i$ are unknowns and $C_0$, $C_f$, UT and P are known and are entered by the operator.

For a value of P less than fifty percent the curve belongs to the family C1 and the following conditions are imposed:

$$C_0 = D/E \text{ per } t=0;$$

$$C_i = \frac{D}{E + F \cdot \frac{DT}{2} + \left(\frac{DT}{2}\right)^2} \text{ for } t = DT/2;$$

$$C_f = \frac{D}{E + F \cdot DT + DT^2} \text{ for } t = DT;$$

$$C_i = C_f + P \cdot \frac{C_0 - C_f}{100} \text{ for } 20 < P < 50.$$

In the four-equation system, D, E, F and $C_i$ are unknowns and $C_0$, $C_f$, DT and P are known and are entered by the operator.

Figure 5:
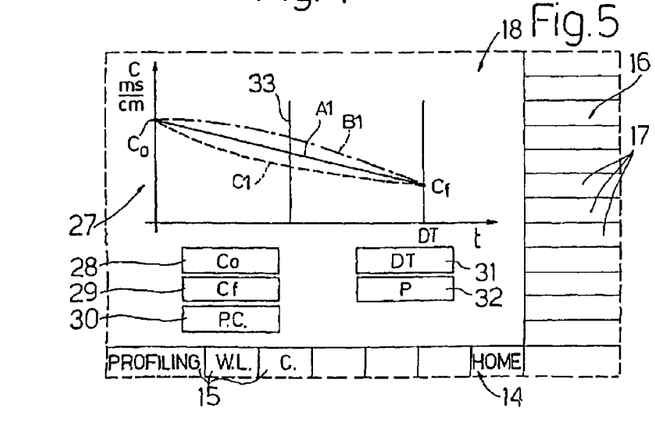

In a similar manner to the preceding case, for each parameter P an image is supplied for the respective curve belonging to one of the families A1, B1 and C1 as illustrated in FIG. 5. All the curves that are displayed satisfy the conditions imposed by the operator, who can select the curve visually that is the most suitable for the patient undergoing the dialysis treatment.

Figure 6:
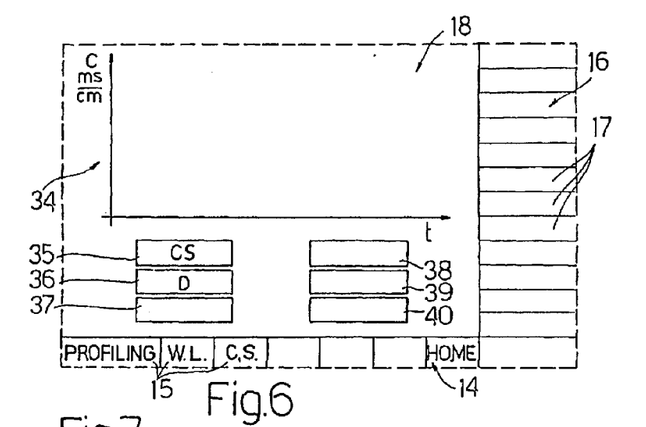
Figure 7:
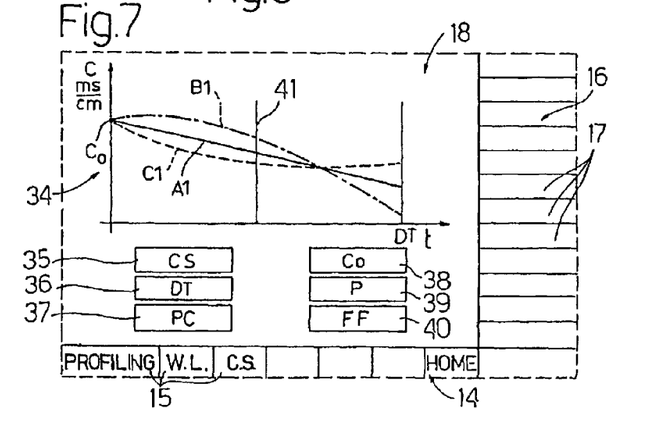

According to the variant in FIGS. 6, and 7, the submenu activated by selecting "SET MODE" offers the options "WL" and "CS", which replaces the "C" mode and provides for stipulating the total quantity of salts that must be transferred to the patient. Selection of option "CS" determines display of the image of FIG. 6, which shows a cartesian system 34 that has an abscissa for plotting the time t, and an ordinate for plotting the electrical conductivity C, a box/touch key 35 for input of data relating to the quantity of salts CS to be transferred to the patient, a box/touch key 36 for entering the dialysis time DT, a box 37 for displaying the progressive curve mode, a box/touch key 38 for entering the initial and maximum conductivity $C_0$, box/touch key 39 for entering discriminating parameter P and a box/touch key 40 for input of a function FF.

Function FF is an absorption function based on algorithms of a known type that make reference to the characteristics of filter 5 and to the equivalent conductivity that is determined on the basis of the general characteristics of a given patient, for whom the dialysis treatment is required.

With variation of parameter P, the curves are for example represented by the curves A1, B1 and C1.

In the case when P is equal to fifty percent, the curve belongs to family A1 and the conditions imposed are as follows:

$$C_i = C_f + \frac{C_0 - C_f}{2};$$

$$C_i = \frac{K \cdot DT}{2} + C_0;$$

$$CS = \int_0^{DT} FF(t) \cdot (K \cdot t + C_0) dt.$$

In the case when P is between fifty and eighty percent, the curve belongs to the family of curve B1 and the conditions imposed are as follows:

$$C_i = A \cdot \left(\frac{DT}{2}\right)^2 + B \cdot \frac{DT}{2} + C_0 \text{ for } t = DT/2;$$

$$C_f = A \cdot DT^2 + B \cdot DT + C_0 \text{ for } t = DT;$$

$$C_i = U_f + P \cdot \frac{C_0 - C_f}{100} \text{ for } 50 < P < 80$$

$$CS = \int_0^{DT} FF(t) \cdot (A \cdot t^2 + B \cdot t + C) \cdot dt$$

In the four-equation system, the unknowns are $C_f$, $C_i$, A and B, whereas P, DT, CS, $C_0$ and the function FF(t) are known.

In the case when P is between twenty percent and fifty percent, the curve belongs to the family of curves C1 and the boundary conditions are as follows:

$C_0 = D/E$ per $t = 0$;

$$C_i = \frac{D}{E + F \cdot \frac{DT}{2} + \left(\frac{DT}{2}\right)^2} \text{ for } t = DT/2;$$

$$C_f = \frac{D}{E + F \cdot DT + DT^2} \text{ for } t = DT;$$

$$C_i = C_f + P \cdot \frac{C_0 - C_f}{100} \text{ for } 20 < P < 50;$$

$$CS = \int_0^{DT} FF(t) \cdot \left(\frac{D}{E + F \cdot t + t^2}\right) \cdot dt.$$

In the five-equation system the unknowns are $C_f$, $C_i$, D, E and F, whereas CS, P, $C_0$, DT and FF(t) are known.

Once the coefficients of the curve corresponding to the assigned value of P are known, microprocessor 11 displays the curve in FIG. 7, and the operator visually monitors the course of the curve with variation of time. On the basis of visual monitoring and the patient's characteristics, the operator alters the value of P if he considers that the course must be corrected, or confirms with hard key 19 of keyboard 12 if the course of the curve is appropriate to the characteristics of a given patient.

Also when determining the conductivity function C(t), the curve is selected from among a group of functions C(t,P) parametrized with parameter P and a subset of functions C(t,P) is selected, imposing the boundary conditions DT, $C_0$ and $C_f$ or CS, FF(t), DT and $C_0$ and, finally, function C(t) is preselected by selecting a defined value of parameter P.

According to another variant, having determined the function U(t) and the respective curve, i.e. the variation of weight loss as a function of time t, the screen shows a touch key 17, which offers the option "MIRRORING" for determining function C(t) and the respective curve, i.e. the variation of the conductivity C as a function of time using only the data that were entered in connection with determination of curve U(t) and two constants M and N, which have previously been entered in the memory of microprocessor 11.

The option "MIRRORING" imposes the condition that the difference between initial flow $U_0$ and final flow $U_f$ expressed in liters/hour is equal to the difference between the initial conductivity $C_0$ and the final conductivity $C_f$ expressed in mS/cm (millisiemens per centimeter) for a known proportionality factor N. This relation is expressed by equation NN:

$[U_0 - U_F]_{l/h} = N \cdot [C_0 - C_f]_{mS/cm}.$

The option "MIRRORING" also stipulates that the initial flow U expressed in liters/hour is equal to the initial conductivity C expressed in mS/cm for a constant M. This relation is expressed by equation MM:

$[U_0]_{l/h} = M \cdot [C_0]_{mS/cm}.$

The option "MIRRORING" further envisages that curve C(t) should have the same qualitative course as curve U(t), i.e. that parameter P should be the same for both curves. Obviously the treatment time DT is the same. Therefore, the values of $C_0$ and $C_f$ can be obtained from equations NN and MM, whereas DT and P are known, and accordingly it is possible to impose the conditions for determining the coefficients of the curve in the manner described previously.

In practice, three different means have been described for determining the course of the function C(t) and of the respective curve. These different means can coexist in the device 6 for setting up the dialysis treatment.

Figure 8:
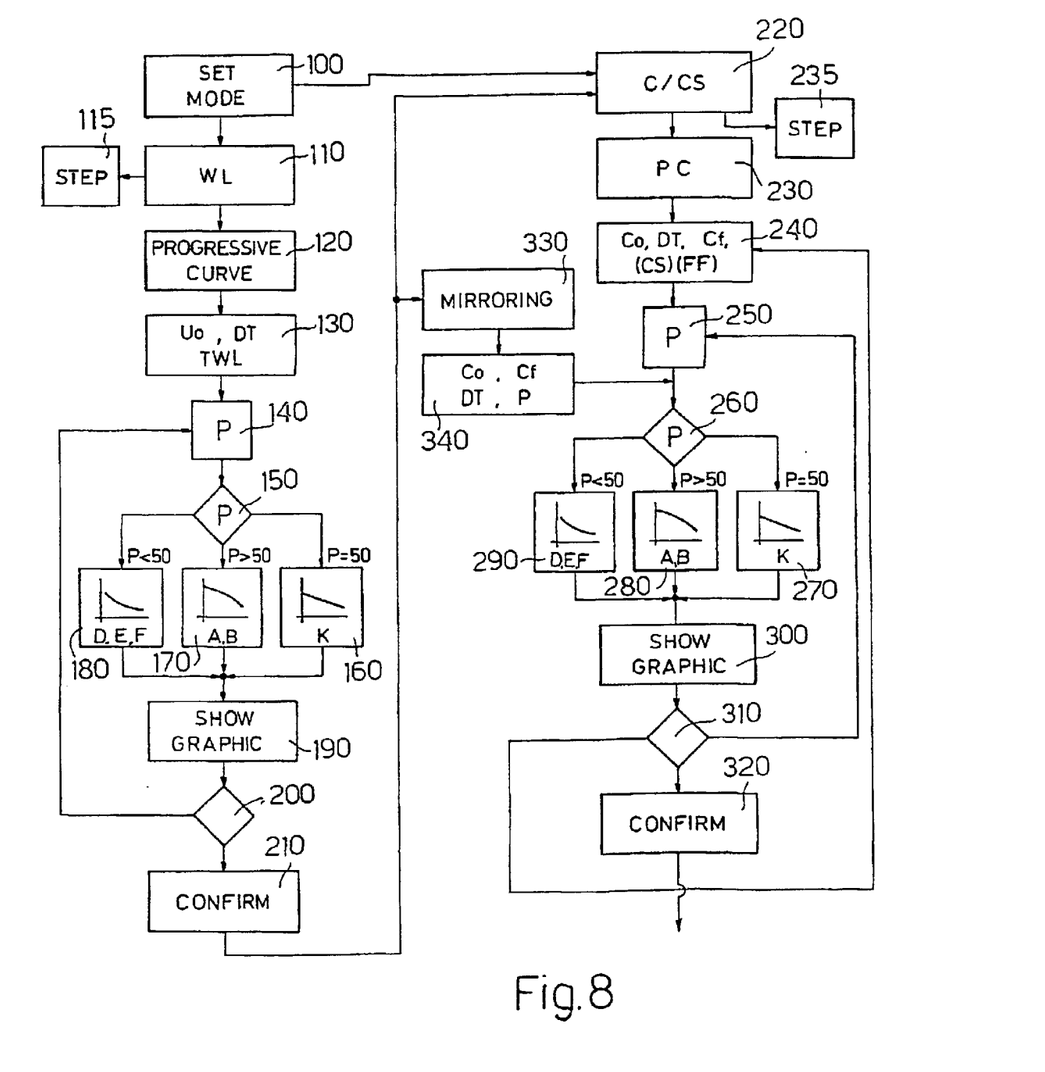
FIG. 8 is a block diagram, showing the operating modes of the machine of FIG. 1 in the stage of setting up of a dialysis treatment.

Referring to FIG. 8, the operations of setting up the dialysis treatment are shown schematically as a block diagram. Block 100 indicates selection of key 19 "SET MODE", which gives access to the options "WL" (block 110), option "C" (CONDUCTIVITY) and CS (CONDUCTIVITY/SALT) grouped in block 220. Selection of option WL gives access to selection between the option "PROGRESSIVE CURVE" (block 120) and the option "STEP CURVE" (block 115). Selection of the option "PROGRESSIVE CURVE" gives access to block 130 for input of data $U_0$, DT and TWL and to block 140 for input/change of P. Assignment of a value of P determines that verification (block 150) of whether P is greater than, equal to or less than 50 is executed. For P equal to 50, microprocessor 11 calculates coefficient K of one of the families of straight lines AA (block 160). For P>50, microprocessor 11 calculates the coefficients A and B of a parabola of family BB (block 170) and for P less than 50, microprocessor 11 calculates the coefficients D, E and F of a hyperbola of family CC (block 180). Once the coefficients of the function corresponding to a given value of P and to a given curve have been calculated, microprocessor 11 displays the curve determined by the value assigned to P on screen 13 with reference to cartesian system 20. Once the curve is displayed, the operator decides (block 200) whether to modify the curve by entering a new value of P (block 140) so that microprocessor 11 repeats the operations shown schematically in the blocks from 150 to 190 for displaying the curve corresponding to the new value assigned to parameter P or for confirming the curve (block 210). Changing of parameter P is repeated until the operator considers that the curve is suitable for setting up the dialysis treatment. Confirmation (block 210) is effected by means of a confirmation key (HARD KEY) 19. Once the curve corresponding to function U(t) has been confirmed, the operator has three options for defining the course of the conductivity function C(t) with variation of time t. Options C and CS have already been described and have been combined in block 220 as they only differ from one another in regard to the data that are entered by the operator. The option "MIRRORING" (block 330) prevents the input of the data as obtained from the data supplied for defining the curve of U(t) and from the constants M and N obtained experimentally. Selection of the option C/CS offers the options "PROGRESSIVE CURVE" and "STEP CURVE". Selection of "PROGRESSIVE CURVE" determines presentation of the input of data (block 240) which, in the case of option "C", are substantially $C_0$ and $C_f$, since DT is known and, in the case of option "CS", are substantially CS, $C_0$ and FF(t), since DT is known. Parameter P is entered (block 250) and compared with the discriminating value 50 (block 260) for determining the coefficients of the functions corresponding to the families of curves A1, B1 and C1. The curve of function C(t) corresponding to the value of P is displayed on screen 13 (block 300) and the operator has the option of deciding (block 310) whether to change the value of P (block 250) and whether to confirm the curve displayed (block 320) by means of a hard key 19.

Selection of the option "MIRRORING" determines calculation of $C_0$ and $C_f$ (block 340), after which calculation of the coefficients of a function C(t) corresponding to a curve belonging to the families A1, B1 and C1, display of the curve and confirmation (blocks from 260 to 320) are effected in the same way as for option C. If the curve displayed by means of the MIRRORING operations does not satisfy the operator, the curve is altered by varying the value of P (block 250) and the microprocessor repeats the operations between blocks 260 and 310.

According to another variant, if the operator considers that some values of the curve do not satisfy the therapeutic requirements he also changes the values of the initial conductivity $C_0$, final conductivity $C_f$ and quantity of salts to be transferred to the patient CS.

In other words, the "MIRRORING" operation is able to supply a curve that is acceptable in itself, or a base curve that is close to the acceptable curve and can be altered for adapting the curve to the therapeutic requirements.

In the example described, the function U(t) of weight loss in unit time corresponds in fact to the delivery Q(t) of the ultrafiltration pump 9 and setting the weight loss means setting the operation of the ultrafiltration pump during the dialysis treatment. According to another variant that is not shown, the extracorporeal circuit is provided with an infusion bag that releases a flow I of infusion fluid into the extracorporeal circuit. In this case the ultrafiltration flow Q is equal to the sum of the weight loss U in unit time and the infusion flow.

What is claimed is:

1. Method of setting up a dialysis treatment in a dialysis machine (1) provided with a device (6) for setting up the dialysis treatment comprising a microprocessor (11), a data input (12, 13) and a screen (13), the method comprising the steps of:

supplying a group of functions (U(t,P); C(t,P)) of a quantity (U; C) characteristic of the dialysis treatment as a function of time (t) and of a variable parameter (P) correlated with intermediate values ($U_i$, $C_i$) of each function (U(t,P); C(t,P)) of the group;

selecting a subset of the group of functions (U(t,P); C(t,P)) imposing boundary conditions ($U_0$, TWL, DT; $C_0$, $C_f$, DT; $C_0$, CS, DT) characteristic of a particular therapy;

assigning values to parameter (P) and displaying the curves corresponding to the functions (U(t,P); C(t,P)) of the subset and to the respective values assigned to parameter (P); and selecting one of the functions ((U(t,P); C(t,P)) of the subset on the basis of the images of the curves.

2. Method according to claim 1, further comprising the steps of:

assigning a value to parameter (P);

displaying the curve corresponding to the function ((U(t, P); C(t,P)) of the subset discriminated by the value assigned to parameter (P);

confirming the value of (P) if the image of the curve complies with defined requirements;

assigning a further value to parameter (P) if the image of the curve does not comply with defined requirements and displaying the further curve corresponding to the further function ((U(t,P); C(t,P)) of the subset discriminated by the further value assigned to parameter (P).

3. Method according to claim 1, in which the parameter (P) is correlated with the curvature of the curves of the respective functions ((U(t,P); C(t,P)) of the group of functions.

4. Method according to claim 3, in which each curve is displayed with respect to a cartesian system (20; 27; 34) on the screen (13), the parameter (P) discriminating whether the curve is a straight line, whether it has curvature in one direction or in the opposite direction, and determining the extent of the curvature.

5. Method according to claim 1, in which the boundary conditions comprise:
at least a first and a second value ($U_0$, TWL; $C_0$, $C_f$; $C_0$, CS) correlated with the quantity (U; C) characteristic of the dialysis treatment;
entering a third value (DT) indicating the duration of the dialysis treatment.

6. Method according to claim 5, in which the machine comprises a blood circuit (4) for circulation of the blood fluid and an ultrafiltration pump (9) for extracting a proportion of the blood fluid and effecting a weight loss (TWL) of the patient, the ultrafiltration pump (9) having a variable delivery (Q(t)), the quantity that is characteristic of the dialysis treatment being the weight loss in unit time (U), the first value ($U_0$) being the hourly weight loss at the beginning of the dialysis treatment, the second value being the total quantity of the blood fluid extracted (TWL), i.e. the weight loss, equal to the integral of the function (U(t)) for the duration of dialysis.

7. Method according to claim 5, in which the machine (1) comprises a dialysate circuit (3) for conveying a dialysate fluid that has a defined concentration of salts and an apparatus (2) for varying the concentration of salts during the dialysis treatment, the quantity being the conductivity (C) of the dialysate, which is correlated with the concentration of salts.

8. Method according to claim 5 or 7, in which the first value is a value of the conductivity ($C_0$) at the beginning of the dialysis treatment, the second value is a value of the conductivity ($C_f$) at the end of the dialysis treatment, the second value being lower than the first value.

9. Method according to claim 5 or 7, in which the first value is a value of the conductivity ($C_0$) at the beginning of the dialysis treatment, the second value being a value of the total quantity of salts (CS) that must be transferred to the patient.

10. Method according to claim 9, in which the quantity of salts is equal to the integral of the curve of the concentration (C(t)) of the dialysate and of the function of an absorption function (FF(t)) that is characteristic of the transfer of salts between the dialysate and the blood fluid.

11. Method according to claim 10, in which the absorption function (FF(t)) is a function of the difference between the concentration of the dialysate and of the characteristics of the blood fluid.

12. Method according to claim 1, comprising the step of determining a first function (U(t)) of a first quantity (U) that is characteristic of the dialysis treatment among a first group of functions (U(t,P)) and a second function (C(t)) of a second quantity (C) that is characteristic of the dialysis treatment among a second group of functions (C(t,P)).

13. Method according to claim 12, in which the first and the second functions (U(t); C(t)) are determined independently of one another.

14. Method according to claim 13, in which each first function (U(t)) of the first group corresponds to a respective first continuous curve in the first derivative and each function (C(t)) corresponds to a respective second continuous curve in the first derivative, the method envisaging selecting the second function (C(t)) stipulating that the second curve should have the same shape as the first curve.

15. Method according to claim 14, in which values of the second function (C(t)) are linked to values of the first function (U(t)) by constants (M, N) determined experimentally.

16. Method according to claim 14, in which the second function (C(t)) is selected among the functions CC(t,P)) of the second group, stipulating the same value of the parameter (P) employed for selecting the first function (U(t)) among the functions (C(t,P)) of the first group.

17. Device for setting up a dialysis treatment comprising a microprocessor, a data input, and a screen, the device being able to perform a method as claimed in claim 1.

18. A machine comprising:
an apparatus for preparing a dialysate;
a dialysate circuit;
a blood circuit; and
a filter connected to the apparatus and the blood circuit, and further comprising a device for setting up a dialysis treatment according to claim 17.

* * * * *

UNITED STATES PATENT AND TRADEMARK OFFICE
CERTIFICATE OF CORRECTION

PATENT NO. : 6,881,344 B2
DATED : April 19, 2005
INVENTOR(S) : Vasta et al.

It is certified that error appears in the above-identified patent and that said Letters Patent is hereby corrected as shown below:

<u>Title page,</u>
Item [57], ABSTRACT,
Line 8, "$(U_1, C_1)$" should read -- $(U_i, C_1)$ --.

<u>Column 12,</u>
Line 29, "$CC(t,P))$" should read -- $(C(t,P))$ --.
Line 32, "$C(t,P))$" should read -- $(U(t,P))$ --.

Signed and Sealed this

Twenty-eighth Day of June, 2005

JON W. DUDAS
*Director of the United States Patent and Trademark Office*